United States Patent
Ferrigato et al.

(10) Patent No.: US 12,297,180 B2
(45) Date of Patent: May 13, 2025

(54) MANUFACTURING OF PROTECTED DO3A

(71) Applicant: BRACCO IMAGING S.P.A., Milan (IT)

(72) Inventors: Aurelia Ferrigato, Trecate (IT); Sonia Gazzetto, Cascinette d'Ivrea (IT)

(73) Assignee: BRACCO IMAGING S.P.A., Milan (IT)

( * ) Notice: Subject to any disclaimer, the term of this patent is extended or adjusted under 35 U.S.C. 154(b) by 491 days.

(21) Appl. No.: 17/784,232

(22) PCT Filed: Dec. 9, 2020

(86) PCT No.: PCT/EP2020/085265
§ 371 (c)(1),
(2) Date: Jun. 10, 2022

(87) PCT Pub. No.: WO2021/116165
PCT Pub. Date: Jun. 17, 2021

(65) Prior Publication Data
US 2023/0040042 A1     Feb. 9, 2023

(30) Foreign Application Priority Data
Dec. 13, 2019   (EP) .................... 19215900

(51) Int. Cl.
*C07D 257/02*       (2006.01)
(52) U.S. Cl.
CPC ................. *C07D 257/02* (2013.01)
(58) Field of Classification Search
CPC ................................ C07D 257/02
See application file for complete search history.

(56) References Cited

U.S. PATENT DOCUMENTS 8,138,332 B2   3/2012   Axelsson et al.

FOREIGN PATENT DOCUMENTS

| EP | 0230893 A2 | 8/1987 |
|---|---|---|
| WO | 9302045 A1 | 2/1993 |
| WO | 2006112723 A1 | 10/2006 |
| WO | 2007106546 A2 | 9/2007 |
| WO | 2016022987 A1 | 2/2016 |
| WO | 2017098038 A1 | 6/2017 |
| WO | 2017098044 A1 | 6/2017 |
| WO | 2018108780 A1 | 6/2018 |

OTHER PUBLICATIONS

Jagadish, Tetrahedron Letters, vol. 52, 2011, 2058-2061. (Year: 2011).*
International Search Report and Written Opinion for PCT/EP2020/085265, mailed Feb. 12, 2021.
Jagadish et al., "On the synthesis of 1,4,7-tris(tert-butoxycarbonylmethyl)-1,4,7, 10-tetraazacyclododecane," Tetrahedron Lett., 52:2058-2061 (2011).
Moore, D. A., "Selective Trialkylation of Cyclen With tert-BUTYL BROMOACETATE [1,4,7,10-Tetraazacyclododecane-1,4,7-triacetic acid, Tri-tert-butyl Ester Hydrobromide]," Org. Synth. 85:10-14 (2008).

* cited by examiner

*Primary Examiner* — D Margaret M Seaman
(74) *Attorney, Agent, or Firm* — VIVICAR Law, PLLC

(57) ABSTRACT

The invention relates to a process for the one-step preparation and isolation of a protected DO3A such as DO3A-tri-tert-butyl ester as a solid salt.

17 Claims, No Drawings

MANUFACTURING OF PROTECTED DO3A

CROSS-REFERENCE TO RELATED APPLICATIONS

This application is the national stage application of corresponding international application number PCT/EP2020/085265, filed Dec. 9, 2020, which claims priority to and the benefit of European application no. 19215900.2, filed Dec. 13, 2019, which is hereby incorporated by reference in its entirety.

FIELD OF THE INVENTION

The present invention relates to the organic chemistry, in particular to the preparation of protected DO3A. More particularly the invention relates to a process for the one-step preparation and isolation of protected DO3A such as DO3A-tri-tert-butyl ester (1,4,7,10-tetraazacyclododecane-1,4,7-triacetic acid tri-tert-butyl ester) as salt.

BACKGROUND OF THE INVENTION

Magnetic Resonance Imaging (MRI) is a renowned diagnostic imaging technique increasingly used in clinical diagnostics for a growing number of indications.

The strong expansion of medical MRI has further benefited from the development of a class of compounds, the MRI contrast agents, that act by causing a dramatic variation of nearby water proton relaxation rates in the tissues/organs/fluids wherein they distribute, thus adding relevant physiological information to the impressive anatomical resolution commonly obtained in the non-contrast MRI images.

Examples of commercially available MRI contrast agents include the complex compounds of the $Gd^{3+}$ ion with linear chelants, such as the DTPA ligand, marketed as MAGNEVIST®; the $Gd^{3+}$ complex of the DTPA-BMA ligand, marketed as OMNISCAN®; the $Gd^{3+}$ complex of BOPTA, known as Gadobenate Dimeglumine and marketed as MultiHance™; and the $Gd^{3+}$ complex compounds with cyclic chelants, such as the DOTA ligand, marketed as DOTAREM®; the $Gd^{3+}$ complex of the hydroxylated tetraaza macrocyclic ligand known as HPDO3A, long time marketed as ProHance® and that of the corresponding butyl-triol derivative, known as Gadobutrol and marketed as Gadavist®.

Key intermediates in the preparation of many of these macrocyclic chelating ligands are the DO3A (1,4,7,10-tetraazacyclododecane-1,4,7-triacetic acid), and the protected derivatives thereof, such as the tri-tert-butyl ester of formula

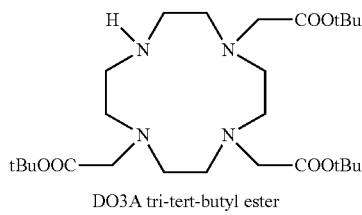

DO3A tri-tert-butyl ester

The preparation of DO3A-tri-tert-butyl ester is commonly carried out by following two main synthetic routes leading to the isolating the product as a free base or, alternatively, as a salt with the anion of the alkylating agent.

The isolation of the product as a hydrobromide has turned out to be preferable in large-scale preparations, as it allows to collect the product in a stable form, that can be conveniently stored for even long periods of time without degradation. When necessary, the hydrobromide salt can then be converted to the corresponding free base prior to its use in subsequent reactions.

Many efforts have thus been made over time to optimize the synthesis and isolation of the DO3A-tri-tert-butyl ester as hydrobromide salt.

WO 93/02045 discloses a procedure for the tris-alkylation of cyclen with tert-butyl bromoacetate in dimethylacetamide in the presence of NaOAc requiring 19 days of reaction time to give the desired hydrobromide with an overall yield of 56%.

A procedure allowing to reduce the reaction time to 60 h is disclosed by Moore in Org. Synth. 2008, 85, 10-14, including the reaction of 1,4,7,10-tetraazacyclododecane and NaOAc with tert-butyl bromoacetate in DMAC and precipitation of the hydrobromide salt of the tri-tert-butyl ester by dilution of the crude reaction with diethyl ether and cooling. A complicated and time-consuming work-up procedure is then required, comprising multiple dissolving, washings and reprecipitations steps, leading to the final product with a yield of 65-80%.

Jagadish et al. (Tetrahedron Lett., 2011, 52 (17), 2058-2061) disclose a procedure that comprises tris-alkylating 1,4,7,10-tetraazacyclododecane with tert-butyl bromoacetate in DMAC (dimethylacetamide) and in the presence of NaOAc for 24 h at room temperature, pouring the reaction mixture in water to give a clear solution, and precipitating the hydrobromide salt by addition of $KHCO_3$. The obtained solid is then collected, dissolved in $CHCl_3$, washed with water, concentrated and re-crystallized by addition of ether, to give the desired product with a yield of about 80%.

U.S. Pat. No. 8,138,332 discloses a manufacturing process that comprises reacting 1,4,7,10-tetraazacyclododecane with tert-butyl bromoacetate in DMAC (dimethylacetamide) and in the presence of NaOAc at room temperature for 5 days, pouring the reaction slurry in a great excess water (3.9:1 (w/w) over the DMAC) to give a clear aqueous solution, adjusting the pH of the solution to 9 with solid $NaHCO_3$, and precipitating the hydrobromide salt of the DO3A-tri-tert-butyl ester by addition of a salt such as KBr to the solution. The hydrobromide salt is collected by filtration with a yield of around 73%.

The above procedures commonly require reaction times of several days, followed by expensive and time-consuming purifications of the crude products, and are, therefore, unsuitable for large-scale productions.

The increasing interest for macrocyclic Gd-based contrast agents such as ProHance and Gadobutrol, and more generally, for DO3A derivatives, makes it highly desirable to have optimized manufacturing procedures that allow to overcome above mentioned drawbacks, and enable a convenient preparation of this important starting material on larger e.g. industrial scale.

SUMMARY OF THE INVENTION

The Applicant has now unexpectedly found that the dilution with water of the raw material obtained by reacting 1,4,7,10-tetraazaciclododecane (or Cyclen, as herein used interchangeably) with an activated acetic ester, such as tert-butyl bromoacetate in an organic solvent and in the presence of a base, makes it possible to isolate the respective DO3A tri-ester as a solid salt directly from the crude reaction.

The present invention generally relates to an improved process for the manufacturing of protected DO3A, such as DO3A-tri-tert-butyl ester, where the compound is collected as a solid salt directly from an organic crude reaction diluted with water.

More particularly, the invention relates to an optimized process for the preparation of DO3A having ester-protected carboxyl groups that essentially comprises diluting with water the crude mixture obtained by reacting 1,4,7,10-tetraazaciclododecane with an activated acetic ester, such as a tert-butyl ester, in an organic solvent and in the presence of an auxiliary base, and then collecting the tri-ester product as a solid salt, directly from the diluted mixture.

Optionally, the process can comprise the addition of supplemental water to the organic solvent in which the reagents are admixed.

An aspect of the invention relates to a one-step process for the manufacturing of a protected DO3A salt of formula (I)

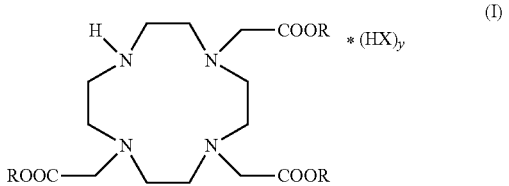

where X is a chlorine, iodine or, preferably, bromine anion; y is an integer from 1 to 3, e.g. 1, 2, or 3, and R is a $C_1$-$C_6$ alkyl or an aryl group;
the process, essentially, comprising:
1) reacting Cyclen with an activated acetic ester of formula $XCH_2COOR$, in an organic solvent and in the presence of an auxiliary base, to give a crude reaction mixture;
2) adding water to the crude mixture of step 1), to obtain a suspension comprising the protected DO3A in the form of a solid salt of formula (I); and
3) collecting and washing the protected DO3A salt.

Organic solvents for use in the reaction of step 1) preferably include dipolar aprotic solvents such as DMF, DMSO MeCN and DMAC. More preferably, the organic solvent is DMAC. The auxiliary base is preferably selected from weak bases such as NaOAc, NaHCO$_3$, Na$_2$CO$_3$, KHCO$_3$, K$_2$CO$_3$, DIPEA, triethylamine; more preferably is NaOAc.

Preferably, in the above formula (I) X is a bromine, and y is 1 or 2; more preferably y is 1. In one embodiment in the above formula (I) R is a benzyl, more preferably, R is a $C_1$-$C_6$ alkyl.

$C_1$-$C_6$ alkyls according to the invention include a linear or branched chain comprising from 1 to 6 carbon atoms such as methyl, ethyl, propyl, iso-propyl, butyl, iso-butyl, tert-butyl, pentyl, hexyl, and the like. Most preferably, in the formula (I) R is tert-butyl.

In an embodiment, the reacting mixture of step 1 further comprises water.

In a preferred embodiment the step 1) of the process comprises reacting 1,4,7,10-tetraazacyclododecane with tert-butyl bromoacetate, for the manufacturing of DO3A protected as tri-tert-butyl ester, such as DO3A-tri-tert-butyl ester mono-hydrobromide salt.

Advantageously, the process of the invention allows to collect DO3A-tri-tert-butyl ester as hydrobromide salt directly from the crude reaction mixture with good yield and optimal purity, that can thus be used as such (or conveniently stored) without needing further complicated and time-consuming purifications or recrystallizations.

DETAILED DESCRIPTION OF THE INVENTION

In one embodiment the present invention relates to a one-step process for the manufacturing of a DO3A-tri-tert-butyl ester salt of formula (IA)

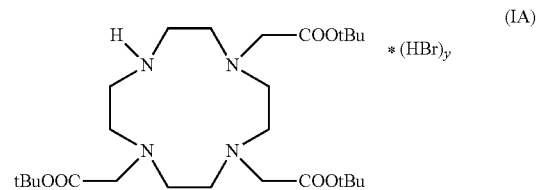

where y is an integer from 1 to 3, preferably from 1 to 2 and, more preferably is 1, that comprises:
1) reacting Cyclen with tert-butyl bromoacetate in an organic solvent and in the presence of an auxiliary base to give a mixture;
2) adding water to the mixture of step 1), to obtain a suspension comprising the DO3A-tri-tert-butyl ester as solid salt of formula (IA); and
3) collecting and washing the DO3A-tri-tert-butyl ester salt.

Step 1

The step 1) of the process comprises reacting Cyclen with tert-butyl bromoacetate, essentially as schematized in the following synthetic scheme 1

Scheme 1

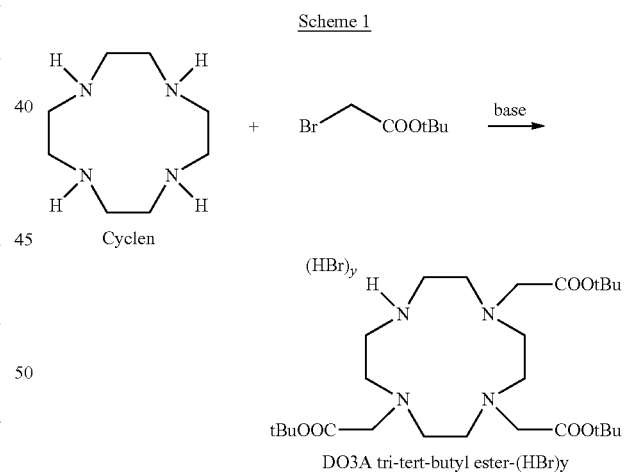

DO3A tri-tert-butyl ester-(HBr)y

This step generally comprises adding tert-butyl bromoacetate to the Cyclen in an organic solvent and in the presence of an auxiliary base to give a mixture comprising DO3A-tri-tert-butyl ester as a solid salt.

For instance, Cyclen and the auxiliary base are first mixed in an organic solvent, to give a mixture that is then loaded with tert-butyl bromoacetate.

In one embodiment, tert-butyl bromoacetate is added in the mixture as such, without any previous dilution thereof.

In a preferred embodiment, the step 1) of the process of the invention comprises i) obtaining a solution of tert-butyl bromoacetate in an organic solvent, and ii) adding the obtained solution to a mixture of Cyclen and an auxiliary base in the same organic solvent. Suitable organic solvents include dipolar aprotic solvents as above said; in a preferred embodiment the organic solvent for use in the process of the invention is DMAC.

For instance, tert-butyl bromoacetate is first diluted with DMAC, e.g. at room temperature, to give a tert-butyl bromoacetate solution with a concentration preferably of from 3 to 7 mol/L (where L refers to the DMAC), more preferably from 3 to 5, and, most preferably, of about 4-5 mol/L.

The obtained solution is then added to a mixture of Cyclen and an auxiliary base in DMAC. Preferably the auxiliary base in the mixture is a weak base; in a preferred embodiment is NaOAc. More typically the mixture is a suspension.

In some embodiments, the mixture of Cyclen and the auxiliary base in DMAC of step 1) may further comprise a certain amount of water (or dilution water).

When present, the amount of dilution water is (by weight) from 0.1 to 2, more preferably from 0.5 to 1.5 times the amount of Cyclen in the mixture. More preferably, it is substantially equal to the amount by weight of Cyclen.

The process preferably comprises preparing a suspension of Cyclen and NaOAc in DMAC (and optionally water) in which the final concentration of the Cyclen is of from 0.5 to 1.0, preferably from 0.6 to 1.0 and, most preferably, from 0.6 to 0.85 mol/L. An amount of tert-butyl bromoacetate is then loaded in the suspension that is sufficient to grant the desired trialkylation of the Cyclen and by avoiding undesired further alkylation.

In one embodiment, the alkylation reaction of step 1) is carried out by using a substantially stoichiometric ratio Cyclen:tert-butyl bromoacetate of 1:3 (mol/mol). In an alternative embodiment, an excess of tert-butyl bromoacetate, e.g. of about 1-30% preferably of 1-10%, corresponding to a Cyclen:tert-butyl bromoacetate ratio of from 1:3 to 1:4 (mol/mol) may be used. Similarly, in one embodiment a substantially stoichiometric ratio between Cyclen and the weak base NaOAc of 1:3 is used, while in alternative embodiments an excess of the base may be used, ranging from 1-30% and preferably of 1-10% over the stochiometric amount.

The proper amount of tert-butyl bromoacetate solution is preferably loaded in the obtained suspension of Cyclen and NaOAc maintained under stirring and at a temperature of from 0 to 25° C.

The addition is conveniently carried out in a time of 1-4 hours, preferably of 2-3 hour.

After the addition, the reaction mixture is maintained under stirring up to completion of the alkylation reaction, e.g. for a time of about 16-48 hours.

In one embodiment, the addition of the tert-butyl bromoacetate and the completion of the reaction are carried out at the same temperature, e.g. ranging from 0 to 25° C., preferably from 5 to 15° C., more preferably from 10 to 15° C., e.g. of about 12° C.; then, the obtained reaction mixture is raised (or maintained) at 25° C. and stirred at this temperature for about 2-4 hours.

In an alternative embodiment, the addition of the tert-butyl bromoacetate is performed at a lower temperature, preferably of from 0 to 15° C., while the completion of the alkylation reaction is carried out at a higher temperature, preferably from 20 to 35° C.

For instance, in one embodiment, the step 1) of the process comprises the addition of a solution of tert-butyl bromoacetate in DMAC to a suspension of Cyclen and NaOAc in the same solvent (and optional water) at a temperature of about 10° C., which is carried out in a time of about 2.5 h, during which the temperature of the reaction mixture is kept at 10-15° C. Then, the obtained reaction mixture is maintained under stirring at this temperature up to completion of the alkylation, for instance for 20-48 h, preferably for 20-30 h, more preferably 20-25. After completion, the temperature of the reaction mixture is preferably raised at room temperature (e.g. about 25° C.) and the mixture is maintained under stirring at this temperature for additional 2-4 hours.

In an alternative embodiment, after the addition of the tert-butyl bromoacetate solution the temperature of the obtained reaction mixture is raised, for example, to 23-35° C. and the mixture is maintained under stirring at this temperature up to completion of the alkylation. Preferably, the reaction mixture is left under stirring at a temperature of 25-30° C. for 20-30 h, preferably for 20-25 h.

Under the above conditions the selective trialkylation of the Cyclen is obtained, with formation of DO3A-tri-tert-butyl ester that remains in suspension as a solid salt, for instance as a mixture of hydrobromides, more typically as mono-hydrobromide.

A crude mixture is thus obtained, typically a suspension or slurry, comprising DO3A-tri-tert-butyl salts (e.g. as hydrobromide), by-product salts (e.g. NaBr), and optional minor amounts of unreacted base and/or organic impurities in the solid suspended phase.

Step 2

Step 2) is conveniently carried out by adding water (also identified herein as "work-up water") to the raw slurry obtained from step 1).

Applicant has indeed unexpectedly found that a suitable addition of water to the slurry collected from step 1) of the process allows to solubilize by-products and unreacted components while leaving the salt (hydrobromide) of the DO3A-tri-tert-butyl ester as essentially the only remaining solid in the resulting crude suspension, which can then be collected.

The amount of water (by weight) to be added to the crude mixture collected from step 1) can suitably be determined e.g. with respect the amount of Cyclen (by weight) subjected to the alkylation reaction.

Suitable amounts of work-up water (by weight) may be e.g. of ten times or less with respect to the amount of starting Cyclen subjected to the alkylation reaction. Such amount of work-up water is generally independent from the presence of optional amounts of water in the initial reaction mixture comprising Cyclen and auxiliary base in DMAC (which optional amounts are nevertheless not more than 2 times the amount of Cyclen).

In a preferred embodiment, the step 2) of the process is carried out by diluting the raw slurry obtained from step 1) with an amount of work-up water which is preferably more than twice (e.g. about 2.5 times) the amount of Cyclen (w/w) undergoing the alkylation reaction. Preferably the amount of water is, by weight, from 3 to 10 times, more preferably from 3 to 8, most preferably from 3 to 6, particularly preferably from 4 to 6, such as about 4, 5 or 6 times the amount of Cyclen (w/w) under reaction.

Indeed, as confirmed by the experimental results, a dilution of the crude suspension obtained from step 1) with an amount of water above 2 times, e.g. corresponding to 2.5-8 times, preferably to 3-8 times the amount (by weight) of the respective starting Cyclen (subjected the trialkylation) allows to solubilize most of unwanted salts/impurities in suspension, while avoids the loss of the desired product, thus leading to achieve the desired product with good yield and purity.

The dilution is typically carried out with purified water, such as Milli-Q or water purified e.g. by reverse osmosis having a temperature of 15-20° C.

Preferably the dilution is carried out at a temperature of 20-25° C., more preferably of about 20° C., and in a time of about 0.5-1 hours, more preferably in about 0.5 h.

In a particularly preferred embodiment, the step 2) of the process comprises diluting the suspension collected from step 1) with an amount of purified water as above said, preferably ranging from 3 to 8, more preferably from 3 to 6 and, most preferably from 4 to 6 times the amount (by weight) of starting Cyclen, in a time of about half an hour and at a temperature of 20-25° C. and, and then maintaining the crude mixture under stirring at about 20° C. for a time of 0.5-3 hours, preferably of about 2 hours.

A suspension is thus obtained, where the solid phase is essentially constituted by the hydrobromide salt of the DO3A-tri-tert-butyl ester and, optionally, minor residual amounts of unwanted reaction salts. The total amount of water in the suspension (i.e. including water added at step 2) and optional water from step 1)) is of at least 2.5 times, more preferably at least 3 times, and even more preferably of at least four times the amount of Cyclen added in step 1) (w/w), up to ten times, preferably up to eight times the amount of Cyclen.

Step 3

The step 3) of the process comprises collecting and then washing the solid product present in the suspension resulting from step 2). The solid can be conveniently collected by using procedures known to the skilled practitioner.

In one embodiment the solid is collected by filtration of the crude suspension.

In an alternative embodiment, that is particularly preferred when working on an industrial scale, the suspension obtained at step 2) of the process is subjected to a centrifugation, allowing to remove, in the liquid phase, residual amounts of DMAC, water, solubilized reaction salts and optional liquid impurities, to obtain a wet solid comprising the crude product as solid salt that is then collected.

The centrifugation is typically carried out at high speed (e.g. between 1800 and 2500 rpm).

The collected cake comprising the crude product is then washed.

Preferably the collected crude product is washed with water (or "washing water").

In one preferred embodiment, the collected wet solid comprising the crude product is washed with an amount of water that, by weight, is from 4 to 20 times the weight of the Cyclen subjected to reaction.

To this extent, the proper amount of water consenting to dissolve and, thus, remove optional residual salts/impurities is preferably determined with reference to the amount of the water added to the raw slurry at step 2) of the process.

Indeed, it is clear to a skilled practitioner that smaller dilutions of the raw mixture in step 2) are preferably associated with washing of the crude product from step 3) with larger amounts of water. Conversely, dilutions using greater quantities of water of the raw mixture, allow to use smaller amounts of wash water.

For instance, as confirmed by the experimental results, when the raw slurry obtained from step 1) of the process is diluted with an amount of work-up water of about 8 times (w/w) the amount (by weight) of starting Cyclen, the crude product collected at the step 3) can be properly washed twice with an amount of washing water each corresponding, by weight, from 2 to 8 times or, more preferably, from 2 to 4 times the amount by weight of the Cyclen, still obtaining a product with optimal purity.

When, instead, the raw slurry is diluted with lower amounts of work-up water, e.g. of about 3-4 times the amount by weight of the Cyclen, the collected crude product is preferably washed twice with higher amount of water, each e.g. ranging from 4 up to 10 or, more preferably, from 4 to 8 times the weight of the starting Cyclen.

In a preferred embodiment the raw slurry obtained from step 1) of the process is diluted with an amount of water that is about 4 times the amount (by weight) of Cyclen, to give a crude product that is then washed twice, each with an amount of water of about 4 times the amount (by weight) of Cyclen, corresponding, in this case, to a ratio organic solvent:total water amount of about 1:1-1:1.1 (w/w).

After washing, the product is collected, e.g. by filtration or centrifugation of the solid, and the wet product is then dried, e.g. at temperatures above room temperature (r.t.) and/or under reduced pressure.

In one preferred embodiment the product is dried at a temperature of 35-40° C. and reduced pressure (e.g. from 5 to 25 mbar) for a time of 20-25 h, to give DO3A-tri-tert-butyl ester as mono-hydrobromide salt with a yield of 73-83%.

While the above description refers specifically to the preparation of the DO3A-tri-tert-butyl ester hydrobromide salt, i.e. a compound of formula (I) where X is a bromine anion and R is tert-butyl, a skilled person is however aware that the disclosed process can be similarly implemented for the preparation of compounds of formula (I)

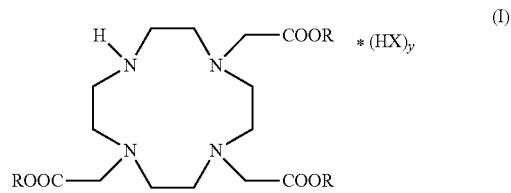

where X is a chlorine, fluorine or iodine anion; y is 2 or 3, and R is a benzyl or, preferably, a $C_1$-$C_6$ alkyl other than tert-butyl.

The use of the process of the invention advantageously allows a significant reduction of both the reaction and work-up times.

For instance, the process of the invention allows to achieve the desired product with a yield of about 83%, or even higher when working on industrial scale, in a reaction time of about 24 hours, that is well below the reaction times required by known procedures.

More in particular, the proposed process allows to obtain DO3A-tri-tert-butyl ester as hydrobromide salt with the above yield and a purity of at least 95%, preferably of at least 97%, more preferably at least 98%, most preferably of at least 99%, e.g. up to 99.5% directly from the crude reaction mixture (obtained by reacting 1,4,7,10-tetraazacyclododecane with tert-butyl bromoacetate in an organic solvent such as DMAC and in the presence of a weak base, such as NaOAc), by simply diluting the crude with water, collecting and washing with water the solid hydrobromide salt. Accordingly, the collected product can advantageously be used as such, without requiring any additional expensive and/or time consuming further purification or reprecipitation or recrystallization step, wherein this renders the process particularly advantageous for productions in large scale, e.g. industrial productions.

The purity of the collected hydrobromide may be determined by different analytical methods, e.g. including NMR vs a standard, confirming the structure and assay of the collected compound, HPLC to determine the purity, and by titration, to determine the optional presence of residual NaBr.

In another aspect, the invention relates to a new process for the manufacturing of a macrocyclic chelating ligand of formula (II)

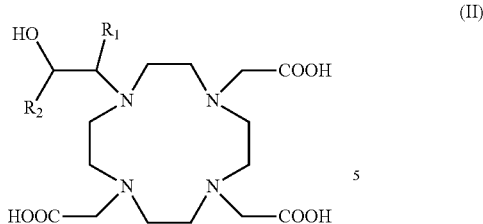

(II)

in which $R_1$ and $R_2$ are both —$CH_2OH$ or $R_1$ is H and $R_2$ is —$CH_3$, or a chelate complex thereof with a paramagnetic metal ion selected in the group consisting of $Fe^{2+}$, $Fe^{3+}$, $Cu^{2+}$, $Cr^{3+}$, $Gd^{3+}$, $Eu^{3+}$, $Dy^{3+}$, $La^{3+}$, $Yb^{3+}$ or $Mn^{2+}$, or an alkaline earth metal ion, or a salt thereof, wherein said process comprises:

a) preparing a hydrobromide salt of the DO3A-tri-tert-butyl ester according to the synthetic process described above;

b) converting the obtained hydrobromide salt into the desired ligand of formula (II); and, c) where applicable, complexing the obtained ligand with a metal ion and isolating the complex.

Preferably the paramagnetic metal ion is $Gd^{3+}$ and the alkaline earth metal ion is $Ca^{2+}$ and the prepared chelate complex is Gadobutrol, Gadoteridol or Calteridol.

More preferably, the metal ion is $Gd^{3+}$ and the prepared chelate complex is Gadoteridol or Gadobutrol of formula

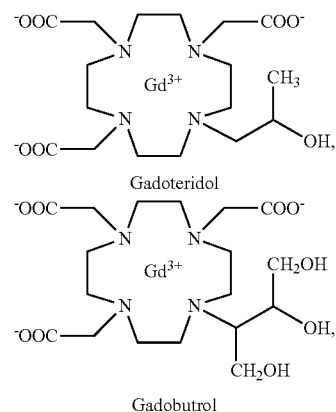

More particularly, in a further aspect the invention relates to a new process for the synthetic preparation of Gadoteridol or Gadobutrol which comprises:

a) preparing DO3A-tri-tert-butyl ester as hydrobromide salt according to the process of the present invention;

b) converting the obtained hydrobromide salt into the desired ligand of formula (II); and c) complexing the obtained ligand with a $Gd^{3+}$ metal ion and isolating the respective Gadoteridol or Gadobutrol complex.

In the above process the step a) comprising the preparation of the DO3A-tri-tert-butyl ester as hydrobromide salt is carried out by the manufacturing process of the instant invention, as extensively reported above, while steps, b) and c) comprehensive of experimental conditions and optional variants thereof, are carried out according to procedure known in the art.

For instance, the step b) may comprise i) the neutralization of the collected hydrobromide salt and its deprotection to give the DO3A ligand where the carboxylic groups are in the deprotected, acidic form; and ii) the alkylation of the DO3A to achieve the desired ligand in the acidic form.

Neutralization and removal of protecting groups from the hydrobromide salt collected from step a) can be carried out according to known techniques, e.g. by hydrolysis in the presence of a base, or treatment with trifluoracetic acid. The alkylation of the obtained DO3A can then be performed, e.g. by using a suitable epoxide as disclosed for instance in EP0988294, to achieve the desired 10-(2-hydroxypropyl)-1,4,7,10-tetraazacyclododecane-1,4,7-triacetic acid (HPDO3A) or [10-[2,3-dihydroxy-1-(hydroxymethyl)propyl]-1,4,7,10-tetraazacyclododecane-1,4,7-triacetic acid (DO3A butyltriol) ligand.

Alternatively, the ligand of formula (II) can be prepared by alkylation in the presence of a base of the hydrobromide salt collected from step a), or of the DO3A-tri-tert-butyl ester collected after neutralization of the salt, performed in a separate step. The alkylation reaction can be carried out according to conventional procedure, e.g. including the reaction of the ester with an optionally protected alkylating group, or with an epoxide e.g. as schematized in the following scheme 1

Scheme 1

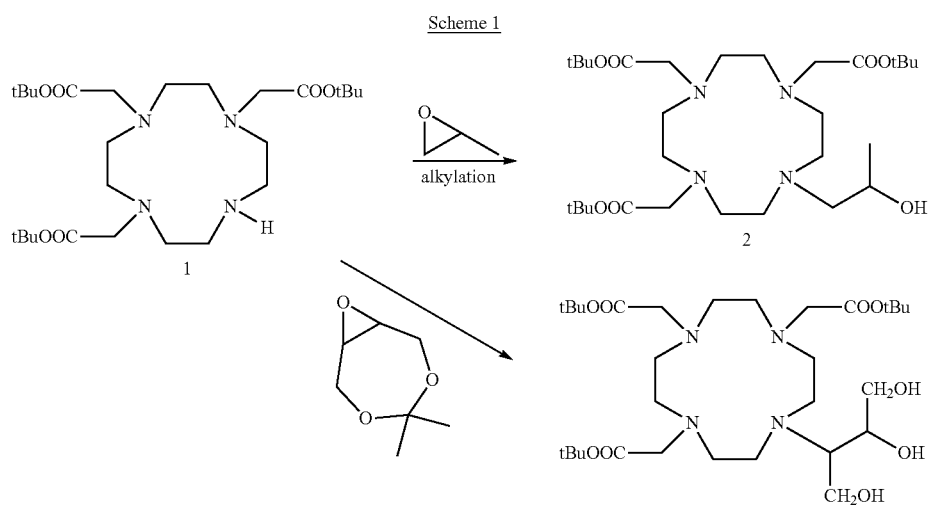

The obtained alkylated ester is then deprotected according to conventional techniques, e.g. by using trifluoroacetic acid, to achieve the respective deprotected ligand.

The step c) of the process comprising the complexation with gadolinium of the ligand obtained from step b) may be performed e.g. by stoichiometric addition of a suitable Gd(III) derivative, particularly a Gd(III) salt or oxide, to a solution of the ligand, e.g. by working according to well-known experimental methods, for instance as reported in EP 230893.

In a further embodiment the invention relates to a new process where the hydrobromide salt of the DO3A-tri-tert-butyl ester obtained according to the method of the invention is used as starting material for the preparation of compounds disclosed in WO 2017/098038, WO2017/098044 or in WO2018/108780.

All starting materials, including solvents, and auxiliary reactants such as NaOAc or other bases used in the process of the invention are commercially available.

Further details on the process of the invention are then reported in the following Experimental Section, constituting a general reference to the operative conditions being employed in a process according to the invention.

EXPERIMENTAL PART
Abbreviations and Definition of Terms

| | |
|---|---|
| DO3A: | 1,4,7,10-tetraazacyclododecane-1,4,7-triacetic acid |
| DO3A tri-tert-butyl ester: | 1,4,7,10-tetraazacyclododecane-1,4,7-triacetic acid 1,4,7-tris(1,1-dimethylethyl) ester |
| DO3A tri-tert-butyl ester-(HBr)$_y$ | 1,4,7,10-tetraazacyclododecane-1,4,7-triacetic acid 1,4,7-tris(1,1-dimethylethyl) ester hydrobromide salt |
| Cyclen | 1,4,7,10-tetraazacyclododecane |
| HPDO3A: | 10-(2-Hydroxypropyl)-1,4,7,10-tetraazacyclododecane-1,4,7-triacetic acid |
| NMR: | Nuclear Magnetic Resonance |
| MRI | Magnetic Resonance Imaging |
| NaOAc | Sodium acetate |
| DMAC | N,N-dimethylacetamide |
| DMF | N,N-dimethylformamide |
| DMSO | Dimethyl sulfoxide |
| MeCN | Acetonitrile |
| CHCl$_3$ | Chloroform |
| NaHCO$_3$ | Sodium hydrogen carbonate |
| Na$_2$CO$_3$ | Sodium carbonate |
| KHCO$_3$ | Potassium hydrogen carbonate |
| K$_2$CO$_3$ | Potassium carbonate |

-continued

EXPERIMENTAL PART
Abbreviations and Definition of Terms

| | |
|---|---|
| DIPEA | N,N-diisopropylethylamine |
| rpm | Revolutions per minute |

HPLC Determination of the Assay of DO3A-tri-tert-butyl-HBr

General Procedure

HPLC Characterization of the Collected DO3A-tri-tert-butyl ester hydrobromide Salt The HPLC characterization of the DO3A-tri-tert-butyl ester hydrobromide salt obtained with the process of the invention was performed with liquid chromatograph Agilent 1100 system. The experimental setup of the HPLC measurements are summarized below.

| Analytical conditions | |
|---|---|
| HPLC system | HPLC equipped with solvent delivery system, autosampler, column thermostat, degasser and diode array detector or variable wavelength detector (or equivalent). |
| Stationary phase: | Zorbax Eclipse XDB-C8, 5 µm, 150 × 4.6 mm |
| Column temperature | 45° C. |
| Mobile phase: | A: 0.01M K$_2$HPO$_4$, 0.017M H$_3$PO$_4$ B: Acetonitrile |

| | Time (min) | % B |
|---|---|---|
| Elution: Gradient | 0 | 5 |
| | 30 | 80 |
| | 35 | 80 |
| | 38 | 5 |
| | 45 | 5 |

| | |
|---|---|
| Flow | 1 mL/min |
| Temperature | 45° C. |
| Detection | UV, 210 nm, Bw = 8 nm; Reference 360 nm, Bw = 100 nm |

| | |
|---|---|
| Injection volume | 10 µL |
| Stop time | 35 min |
| Reference peak | DO3A 3tBu |
| Retention time | DO3A 3tBu ≅ 14.5 min. |

Determination of the Bromide Assay in DO3A-tri-tert-butyl-HBr.

General Procedure

The determination of bromide ions content in the collected DO3A tri-t-butyl HBr is performed by potentiometric titration using 0.1N silver nitrate solution with an Ag/AgCl combined electrode, according to known procedures.

Example 1: Synthesis of DO3A-Tri-Tert-Butyl Ester Mono Hydrobromide Salt

Work-Up Water 4× and Washing Water 2(4×) (w/w) Over Starting Cyclen

The synthesis is carried out according to the following synthetic scheme

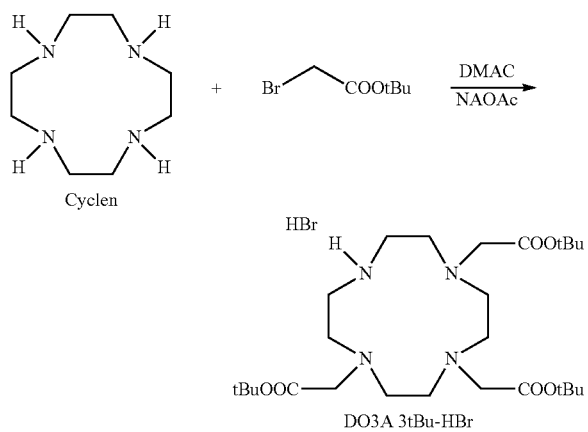

To a suspension of commercially available 1,4,7,10-tetraazacyclododecane (15.1 kg; 87.65 mol; conc.=0.83 mol/L of DMAC) and sodium acetate (22.65 kg; 276.11 mol) in DMAC (99 kg; 105.3 L), a solution of tert-butyl bromoacetate (53.87 kg; 276.11 mol; conc=4.88 mol/L of DMAC) in DMAC (53.23 kg; 56.63 L) was added at 10° C. during 2.5 h. Then the temperature was raised to 25° C. and the mixture was stirred for 24 h. Water (60.0 kg; 4:1 w/w over starting Cyclen) was then added in 0.5 h. After 2 h the mixture was centrifuged, and the collected cake was washed with water (2×60.0 Kg=2×4:1 w/w over starting Cyclen). The wet solid was dried under vacuum obtaining 38.43 kg of the desired hydrobromide salt as a white powder.

Yield: 73.5% yield.
Title HPLC: (against standard) is 100%
Title NMR: (against standard) 99.86%
Bromine assay: 100.7%

Example 2: Synthesis of DO3A-Tri-Tert-Butyl Ester Hydrobromide Salt

Work-Up Water 4× and Washing Water 5.3×+4× (w/w) Over Starting Cyclen

Cyclen (9 kg; 52.24 mol; 0.83 mol/L of DMAC) and sodium acetate (13.5 kg; 164.57 mol) in DMAC (59.3 kg; 63.1 L) were loaded in a reactor. The resulting suspension is maintained under stirring for 30 min at 25° C. The suspension is then cooled at 10° C. and added with a solution of tert-butyl bromoacetate (32.1 kg; 164.57 mol; 4.85 mol/L of DMAC) in DMAC (31.9 kg; 33.9 L) during 3 h. The pipeline is washed with DMAC (2.15 kg; 2.29 L) that is then added to the reaction mixture. Then the temperature was raised to 25° C. and the mixture was stirred for 24 h. Water (36.1 kg; 4:1 w/w over starting Cyclen) was then added in 0.5 h and after 2 h the mixture was centrifuged, and the cake was washed with water (47.4 kg+36.5 kg). The wet solid was dried under vacuum obtaining 22.70 kg of the hydrobromide salt.

Yield: 72.8%.
Title HPLC: (against standard) is 100%
Title NMR: (against standard) 99.86%
Bromine assay: 100.6%

Example 3: Synthesis of DO3A-Tri-Tert-Butyl Ester Hydrobromide Salt

Work-Up Water 4× and Washing Water 2(4×) (w/w) Over Starting Cyclen

Cyclen (9 kg; 52.24 mol; 0.83 mol/L of DMAC) and sodium acetate (13.5 kg; 164.57 mol) in DMAC (59.15 kg; 62.93 L) were loaded in a reactor. The resulting suspension is maintained under stirring for 30 min at 25° C. The suspension is then cooled at 10° C. and added with a solution of tert-butyl bromoacetate (32.14 kg; 164.74 mol; 4.86 mol/L of DMAC) in DMAC (31.85 kg; 33.88 L) during 3 h. The pipeline is washed with DMAC (2.15 kg; 2.29 L) that is then added to the reaction mixture. Then the temperature was raised to 25° C. and the mixture was stirred for 24 h. Water (36 kg) was then added in 0.5 h and after 2 h the mixture was centrifuged, and the cake was washed with water (36.7 kg+36.8 kg). The wet solid was dried under vacuum obtaining 24.16 kg of the hydrobromide salt.

Yield: 76.7%.
Title HPLC: (against standard) is 100%
Title NMR: (against standard) 98.84%
Bromine assay: 99.9%

Example 4: Synthesis of DO3A-Tri-Tert-Butyl Ester Hydrobromide Salt

Work-Up Water 4× (w/w) and Washing Water 2(4×) (w/w) Over Starting Cyclen

Cyclen (10.0 g; 58.05 mmol) and sodium acetate (17.9 g; 217.68 mmol) in DMAC (72.5 mL) were loaded in a reactor. The resulting suspension was maintained under stirring (250 rpm) for 30 min at 25° C. The suspension was then cooled at 12° C. and added with a solution of tert-butyl bromoacetate (42.5 g; 217.68 mmol) in DMAC (37.5 mL) at 12° C. during 1.5 h. The mixture was stirred for 24 h at this temperature, then it was heated to 25° C. and stirred for 2 h at this temperature. After cooling at about 18-20° C. water (40 mL) was added in 0.25 h and after 1 h the mixture was filtered on porous septum P3 and washed with water (40 ml+40 mL). The wet solid was dried under vacuum.

Yield: 82.9%
HPLC Area %: 99.2%
Title NMR (against standard): 97.6%
Bromine assay: 102.0%

Example 5: Synthesis of DO3A-Tri-Tert-Butyl Ester Hydrobromide Salt

Dilution Water 1×, Work-Up Water 8× and Washing Water 2(2×) (w/w) Over Starting Cyclen Cyclen (10.0 g; 58.05 mmol) and sodium acetate (17.9 g; 217.68 mmol) in DMAC (72.5 mL) were loaded in a reactor. The resulting suspension was maintained under stirring (250 rpm) for 30 min at 25° C. The suspension was then cooled at 12° C. and added with water (10 mL). Maintaining the temperature at 12° C. a solution of tert-butyl bromoacetate (42.5 g; 217.68 mmol) in DMAC (37.5 mL) was added during 2.25 h. The mixture was stirred for 24 h at this temperature, then it was heated to 25° C. and stirred for 2 h at this temperature. After cooling at about 18-20° C. water (80 mL) was added in 0.5 h and after 1 h the mixture was filtered on porous septum P3 and washed with water (20 mL+20 mL). The wet solid was dried under vacuum.

Yield: 80.4%

HPLC Area %: 98.1%

Title NMR (against standard): 97.7%

Bromine assay: 103.6%

Example 6: Synthesis of DO3A-Tri-Tert-Butyl Ester Hydrobromide Salt

Dilution Water 1×, Work-Up Water 8× and Washing Water 2(2×) (w/w) Over Starting Cyclen Cyclen (10.0 g; 58.05 mmol) and sodium acetate (16.7 g; 203.17 mmol) in DMAC (72.5 mL) were loaded in a reactor. The resulting suspension was maintained under stirring (250 rpm) for 30 min at 25° C. The suspension was then cooled at 0° C. and added with water (10 mL). Maintaining the temperature at 0° C. a solution of tert-butyl bromoacetate (39.6 g; 203.17 mmol) in DMAC (37.5 mL) was added during 2.25 h. The mixture was stirred for 24 h at this temperature, then it was heated to 25° C. and stirred for 2 h at this temperature. After cooling at about 18-20° C. water (80 mL) was added in 0.5 h and after 1 h the mixture was filtered on porous septum P3 and washed with water (20 mL+20 mL). The wet solid was dried under vacuum.

Yield: 77.3%

HPLC Area %: 98.3%

Title NMR (against standard): 97.5%

Bromine assay: 106.9%

Example 7: Synthesis of DO3A-Tri-Tert-Butyl Ester Hydrobromide Salt

Work-Up Water 2× and Washing Water 2(2×) (w/w) Over Starting Cyclen

Cyclen (10.0 g; 58.05 mmol) and sodium acetate (15.0 g; 182.85 mmol) in DMAC (72.5 mL) were loaded in a reactor. The resulting suspension was maintained under stirring (250 rpm) for 30 min at 25° C. The suspension was then cooled at 10° C. and added with a solution of tert-butyl bromoacetate (35.7 g; 182.85 mmol) in DMAC (38.0 mL) at 11° C. during 2.5 h. Then the temperature was raised to 25° C. in 1 h and the mixture was stirred for 24 h at this temperature. After cooling at about 18-20° C. water (20 mL) was added in 0.5 h and after 2 h the mixture was filtered on porous septum P3 and washed with water (20 mL+20 mL). The wet solid was dried under vacuum.

Yield: 72.6%

HPLC Area %: 99.0%

Title NMR (against standard): 95.9%

Bromine assay: 104.3%

Example 8: Assessment of the Effect of the Water Amount

To determine suitable amounts of water to be added to the crude slurry obtained by reaction of 1,4,7,10-tetraazaciclododecane with tert-butyl bromoacetate in DMAc and NaOAc, tests were carried out using 10 g of starting Cyclen, same amounts of DMAc (110 ml total amount) and tert-butyl bromoacetate, fixed tert-butyl bromoacetate:Cyclen ratio and variable amounts of work-up/washing water.

Cyclen (10.0 g; 58.05 mmol) and sodium acetate (15.0 g; 182.85 mmol) in DMAC (72.5 mL) were loaded in a reactor. The resulting suspension is maintained under stirring (250 rpm) for 30 min at 25° C. The suspension is then cooled at 10° C. and added with a solution of tert-butyl bromoacetate (35.7 g; 182.85 mmol) in DMAC (37.5 mL) at 10° C. during 2.5 h. Then the temperature was raised to 25° C. in 1 h and the mixture was stirred for 24 h at this temperature. After cooling at about 18-20° the amount of water was added (see the following table) in 0.5 h and after 2 h the mixture was filtered on porous septum P3 and washed with water. The wet solid was dried under vacuum. The results of the different tests carried out with different quantities of work-up and wash water (the amounts of water are provided as parts by weight, with reference to the amount of starting Cyclen) are shown in the following table 1, where the purity of the collected product is provided as HPLC (area %) and title NMR (vs standard).

TABLE 1

| Test | Work-up Water* | Washing Water* | Yield (%) | HPLC (area %) | NMR assay |
|---|---|---|---|---|---|
| 1 | 4 | 4 × 2 | 75.1 | 99.4 | 96.1$^a$ |
|   |   |       | 76.7$^b$ | 100$^b$ | 98.8$^b$ |
| 2 | 8 | 8 × 2 | 66.9 | 99.0 | 97.0$^a$ |
| 3 | 8 | 2 × 2 | 67.6 | 99.2 | 96.4$^a$ |
| 4 | 2 | 2 × 2 | 64.0 | 98.8 | 90.6$^a$ |
| 5 | 6 | 3 × 2 | 73.8 | 98.4 | 96.0$^a$ |
| 6 | 2 | 2 × 2 | 72.6 | 99.0 | 95.9$^a$ |
| 7 | 3 | 4 × 2 | 68.3 | 98.8 | 98.0$^a$ |

$^a$laboratory scale
$^b$pilot plant scale, example 3
*parts by weight with respect to the amount of Cyclen

RESULTS

Although they have been obtained with tests carried out on a laboratory scale (resulting in washing and filtration less efficient than those obtained in a pilot or industrial plant), the results reported in the above table confirm that the identified working conditions allow to isolate the desired product with good yield, and an optimal purity degree, exceeding 95%, enabling its use as such, without requiring additional work-up or purification.

The invention claimed is:

1. A one-step process for a preparation of a protected DO3A salt of formula (I)

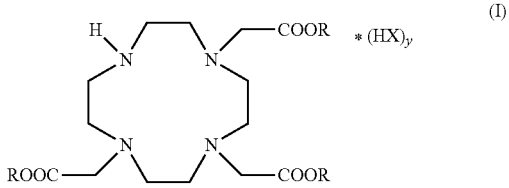

where:
- X is a chlorine, iodine or bromine anion;
- y is an integer from 1 to 3; and
- R is a $C_1$-$C_6$ alkyl or an aryl group; said process comprising:
  1) Reacting Cyclen with an activated acetic ester of formula $XCH_2COOR$, in an organic solvent and in the presence of an auxiliary base, to give a mixture;
  2) Adding water to the mixture of step 1) in an amount by weight of ten times or less with respect to the amount of Cyclen, to obtain a suspension comprising protected DO3A as a solid salt of formula (I); and
  3) Collecting and washing the protected DO3A salt.

2. The process of claim 1 wherein the mixture of step 1) further comprises water.

3. The process of claim 2 wherein the water in the mixture of step 1) is in an amount of from 0.1 to 2 times the amount of Cyclen (w/w).

4. The process of claim 1 wherein in the formula (I) X is bromine, and R is tert-butyl.

5. The process of claim 1 wherein in step 1) the organic solvent is DMAC, and the auxiliary base is NaOAc.

6. The process of claim 5 wherein the reaction of step 1) is carried out by using a ratio Cyclen:tert-butyl bromoacetate and Cyclen:NaOAc from 1:3 to 1:4 (mol/mol).

7. The process of claim 6 wherein the ratio Cyclen:tert-butyl bromoacetate and Cyclen:NaOAc is from 1:3 to 1:3.3.

8. The process of claim 5 wherein the step 1) of the process comprises:
  i) obtaining a solution of tert-butyl bromoacetate in DMAC;
  ii) adding the obtained solution to a suspension of Cyclen and NaOAc in DMAC.

9. The process of claim 8 wherein the concentration of the tert-butyl bromoacetate in the solution is of from 3 to 5 mol/L, and that of the Cyclen in the suspension is of from 0.5 to 1.0 mol/L.

10. The process of claim 8 wherein the tert-butyl bromoacetate solution is added to the suspension of Cyclen and NaOAc stirred at a temperature of 0-25° C.

11. The process of claim 10 wherein the suspension of Cyclen and NaOAc in DMAC is stirred at a temperature of 0-15° C.

12. The process according to claim 1, wherein the water added in step 2) is in an amount of 2.5-10 times (w/w) with respect to the amount of Cyclen in step 1).

13. The process of claim 1 wherein the step 3) comprises collecting the protected DO3A salt of formula (I) obtained from step 2) and washing the collected salt with water.

14. The process of claim 13 wherein the protected DO3A salt is collected by filtration or centrifugation.

15. The process of claim 13 wherein the amount of washing water is from 4 to 20 times the amount of Cyclen in step 1) (w/w).

16. The process of claim 1 wherein the collected protected DO3A salt is DO3A-tri-tert-butyl ester mono hydrobromide.

17. The process of claim 16 wherein the DO3A-tri-tert-butyl ester mono hydrobromide has a purity of at least 95%.

* * * * *